US010060842B2

(12) United States Patent
McMillon et al.

(10) Patent No.: US 10,060,842 B2
(45) Date of Patent: Aug. 28, 2018

(54) DOWNHOLE VISCOSITY SENSOR WITH SMART FLUID

(71) Applicant: HALLIBURTON ENERGY SERVICES, INC., Houston, TX (US)

(72) Inventors: Christopher Michael McMillon, Wylie, TX (US); Robert Mitchell Neely, Carrollton, TX (US)

(73) Assignee: HALLIBURTON ENERGY SERVICES, INC., Houston, TX (US)

( * ) Notice: Subject to any disclaimer, the term of this patent is extended or adjusted under 35 U.S.C. 154(b) by 237 days.

(21) Appl. No.: 15/039,023

(22) PCT Filed: Dec. 24, 2013

(86) PCT No.: PCT/US2013/077704
§ 371 (c)(1),
(2) Date: May 24, 2016

(87) PCT Pub. No.: WO2015/099714
PCT Pub. Date: Jul. 2, 2015

(65) Prior Publication Data
US 2017/0038287 A1    Feb. 9, 2017

(51) Int. Cl.
*G01N 11/04* (2006.01)
*E21B 49/08* (2006.01)
*E21B 47/10* (2012.01)
*E21B 49/00* (2006.01)

(52) U.S. Cl.
CPC .............. *G01N 11/04* (2013.01); *E21B 47/10* (2013.01); *E21B 49/001* (2013.01); *E21B 49/08* (2013.01); *E21B 2049/085* (2013.01)

(58) Field of Classification Search
CPC ....... G01N 11/04; E21B 47/10; E21B 49/001; E21B 49/08; E21B 2049/085
USPC .......................................................... 73/54.05
See application file for complete search history.

(56) References Cited

U.S. PATENT DOCUMENTS

| 4,067,230 A | * | 1/1978 | Ball ........................ G01N 11/14 73/196 |
| 4,155,253 A | * | 5/1979 | Kato ........................ G01F 1/10 415/104 |
| 6,609,431 B1 | | 8/2003 | Tietsworth et al. |
| 6,959,773 B2 | | 11/2005 | Mese et al. |
| 7,437,912 B2 | | 10/2008 | Sparks et al. |
| 8,104,329 B2 | | 1/2012 | Colin et al. |

(Continued)

OTHER PUBLICATIONS

International Search Report and Written Opinion, dated Sep. 22, 2014, 11 pages, Korean Intellectual Property Office.

*Primary Examiner* — Son Le
*Assistant Examiner* — Marrit Eyassu

(57) ABSTRACT

A downhole viscosity sensor and related systems and methods are disclosed. The sensor includes a first fluid flow path including a turbine and a velocity sensor, a second fluid flow path including a second turbine and a second velocity sensor, a mechanical or electrical linkage linking the first turbine and second turbine to cause the turbines to rotate in unison. The sensor also includes a field generator, which may be a magnetic field or electric field generator. The first fluid flow path includes an open flow path for receiving a fluid from a formation and the second fluid flow path includes a closed flow path having a reference fluid that has a variable but known viscosity.

20 Claims, 5 Drawing Sheets

(56) References Cited

U.S. PATENT DOCUMENTS

| | | |
|---|---|---|
| 8,443,875 B2 | 5/2013 | Lee |
| 9,879,519 B2* | 1/2018 | Roberson ................ E21B 47/00 |
| 2003/0052672 A1 | 3/2003 | Speier et al. |
| 2005/0028522 A1 | 2/2005 | Fripp et al. |
| 2005/0223808 A1 | 10/2005 | Myers et al. |
| 2008/0047753 A1 | 2/2008 | Hall et al. |
| 2010/0206063 A1* | 8/2010 | Fujisawa ................ E21B 49/10 |
| | | 73/152.24 |
| 2012/0086456 A1 | 4/2012 | Kumar |
| 2012/0118638 A1 | 5/2012 | Orbell et al. |
| 2015/0027781 A1* | 1/2015 | Vestavik ................ E21B 21/08 |
| | | 175/57 |

\* cited by examiner

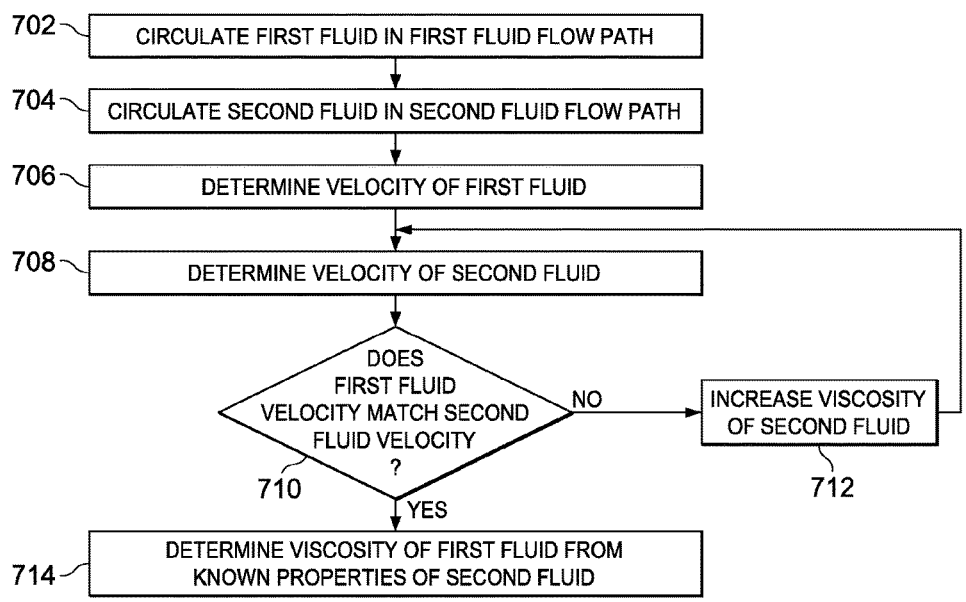
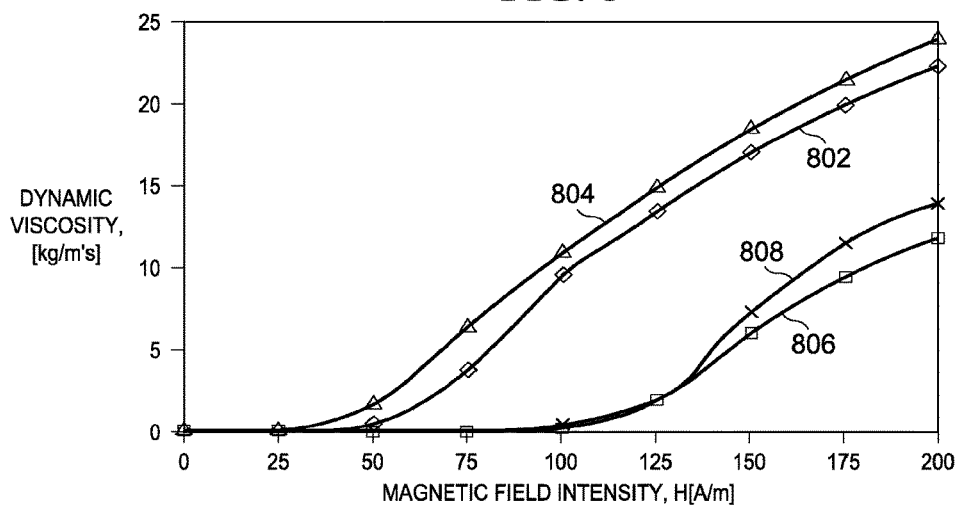

DOWNHOLE VISCOSITY SENSOR WITH SMART FLUID

CROSS-REFERENCE TO RELATED APPLICATIONS

This application is a U.S. national stage patent application of International Patent Application No. PCT/US2013/077704, filed on Dec. 24, 2013, the benefit of which is claimed and the disclosure of which is incorporated herein by reference in its entirety.

FIELD OF THE INVENTION

The disclosure relates to oil and gas exploration and production, and more particularly, but not by way of limitation to downhole systems, apparatuses, and methods for determining the viscosity of a fluid in a wellbore.

DESCRIPTION OF RELATED ART

Crude oil and natural gas occur naturally in subterranean deposits and their extraction includes drilling a well. The well provides access to a production fluid that often contains crude oil and natural gas. In the course of drilling or producing a well it is often desirable to know as much as possible about the production fluid.

BRIEF DESCRIPTION OF THE DRAWINGS

FIG. 7 is a flow chart showing an illustrative process for using the system of FIG. 5 to determine the viscosity of a downhole fluid; and FIG. 8 is a flow chart showing an illustrative process for using the system of FIG. 5 to determine the viscosity of a downhole fluid.

DETAILED DESCRIPTION OF ILLUSTRATIVE EMBODIMENTS

Figure 1:
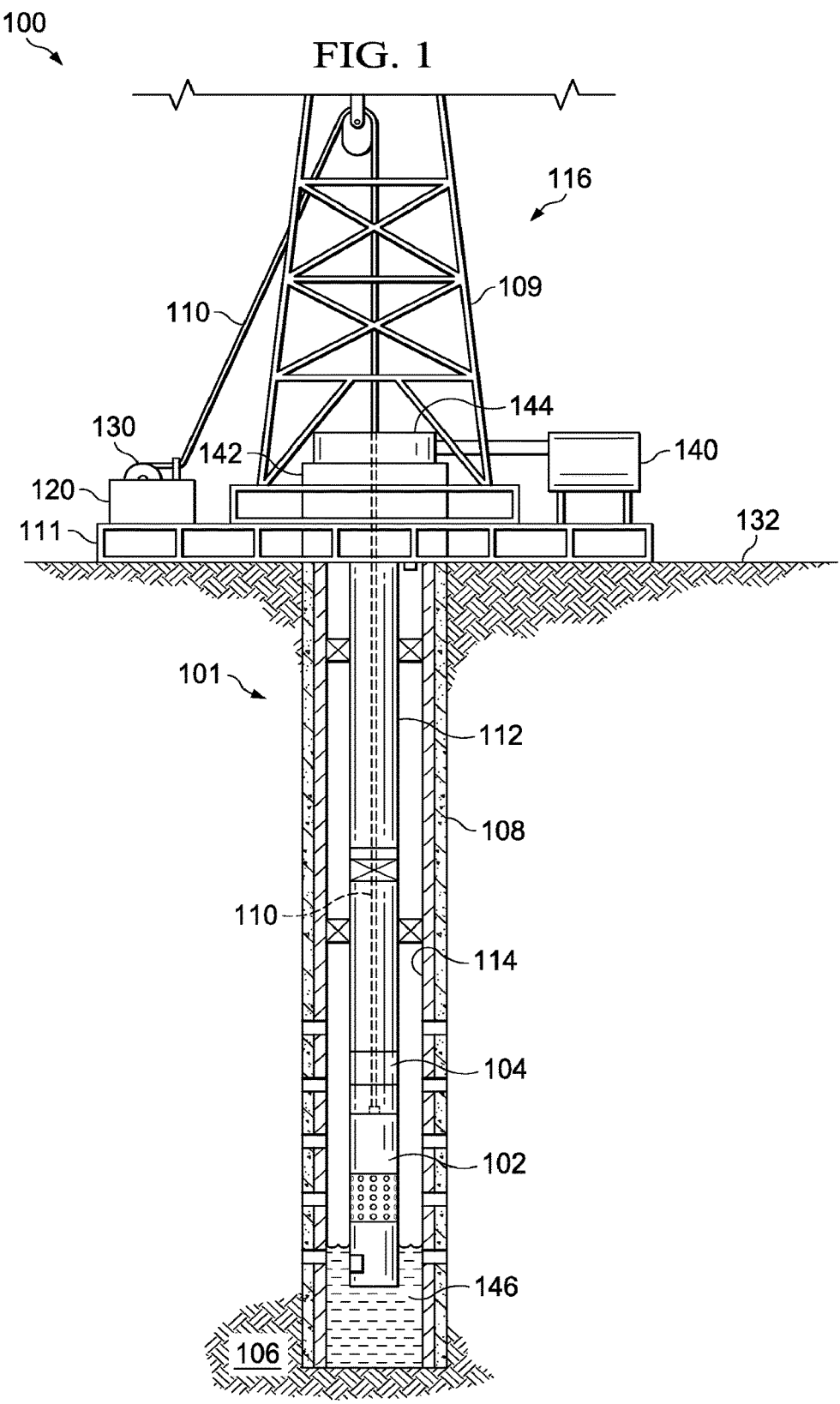
FIG. 1 illustrates a schematic view of a producing well in which a system for determining the viscosity of a downhole fluid is deployed.

In the following detailed description of the illustrative embodiments, reference is made to the accompanying drawings that form a part hereof. These embodiments are described in sufficient detail to enable those skilled in the art to practice the invention, and it is understood that other embodiments may be utilized and that logical structural, mechanical, electrical, and chemical changes may be made without departing from the scope of the invention. To avoid detail not necessary to enable those skilled in the art to practice the embodiments described herein, the description may omit certain information known to those skilled in the art. The following detailed description is, therefore, not to be taken in a limiting sense, and the scope of the illustrative embodiments is defined only by the appended claims.

In the drawings and description that follow, like parts are typically marked throughout the specification and drawings with the same reference numerals, respectively. The drawing figures are not necessarily to scale. Certain features of the invention may be shown exaggerated in scale or in somewhat schematic form and some details of conventional elements may not be shown in the interest of clarity and conciseness.

The embodiments described herein relate to systems, tools, and methods for estimating or determining the viscosity of a fluid in a wellbore, which may be referred to as a production fluid. In one illustrative embodiment, a downhole tool and system operate to estimate the viscosity of the production fluid by comparing flow characteristics of the production fluid to the flow characteristics of a reference fluid. By utilizing a viscosity-tunable fluid having known rheological properties as the reference fluid, the viscosity of the tunable fluid may be manipulated until the flow characteristics are approximately equivalent, which may indicate that the viscosity of the production fluid is approximately the same as the viscosity of the reference fluid at the time of equivalence.

Unless otherwise specified, any use of any form of the terms "connect," "engage," "couple," "attach," or any other term describing an interaction between elements is not meant to limit the interaction to direct interaction between the elements and may also include indirect interaction between the elements described. In the following discussion and in the claims, the terms "including" and "comprising" are used in an open-ended fashion, and thus should be interpreted to mean "including, but not limited to". Unless otherwise indicated, as used throughout this document, "or" does not require mutual exclusivity.

The various characteristics mentioned above, as well as other features and characteristics described in more detail below, will be readily apparent to those skilled in the art with the aid of this disclosure upon reading the following detailed description of the embodiments, and by referring to the accompanying drawings. Other means may be used as well.

Referring now to the figures, FIG. 1 shows an example of a production system 100 that includes diagnostic functionalities for determining the viscosity of a production fluid, which may be a fluid extracted from a geological formation 106 surrounding a wellbore 108. The production system 100 includes a rig 116 atop the surface 132 of a well 101. Beneath the rig 116, the wellbore 108 is formed within the geological formation 106, which is expected to produce hydrocarbons. The wellbore 108 may be formed in the geological formation 106 using a drill string that includes a drill bit to remove material from the geological formation 106. The wellbore 108 in FIG. 1 is shown as being near-vertical, but may be formed at any suitable angle to reach a hydrocarbon-rich portion of the geological formation 106. As such, in an embodiment, the wellbore 108 may follow a vertical, partially vertical, angled, or even a partially horizontal path through the geological formation 106.

Following or during formation of the wellbore 108, a casing 114 may be installed and perforated to support the wellbore 108 and to allow ingress of production fluids at desired locations. To draw production fluids to the surface 132, a production tool string 112 may be deployed that includes tools for use in the wellbore 108 to operate and maintain the well 101. For example, the production tool string 112 optionally includes an artificial lift system to assist fluids from the geological formation to reach the surface 132 of the well 101. Such an artificial lift system may include an electric submersible pump 102, sucker rods, a gas lift system, or any other suitable system for generating a pressure differential. The pump 102 receives power from the surface 132 from a power transmission cable 110, which may also be referred to as an "umbilical cable." A downhole viscosity sensor 104 may be similarly deployed or otherwise included in the production tool string 112 to estimate the viscosity of production fluid 146.

In such systems, a well operator may monitor the condition of the well 101 and components of the production tool string 112 to ensure that the well operates efficiently and to determine whether the production fluid 146 has desired properties. For example, an operator may want to determine that the production fluid 146 has a high hydrocarbon content and a low water content. As described in more detail below, one way to estimate the composition of the production fluid 146 may be to determine its viscosity, since fluids of different compositions of production fluid 146 will generally have different viscosities.

In an embodiment, a controller 120 may be communicatively coupled to the downhole viscosity sensor 104 by the cable 110 or by a wireless communication protocol, such as mud-pulse telemetry or a similar communications protocol. The cable 110 may supply power to the downhole viscosity sensor 104 and facilitate the transmission of data to and from the controller 120. In another embodiment, the downhole viscosity sensor 104 may be permanently or semi-permanently deployed in the wellbore 108, and may include an on-board controller that communicates with the surface controller 120 via a wired or wireless communications protocol.

The downhole viscosity sensor 104 is deployed from the rig 116, which may be a drilling rig, a completion rig, a workover rig, or another type of rig. The rig 116 includes a derrick 109 and a rig floor 111. The production tool string 112 extends downward through the rig floor, through a fluid diverter 144 and blowout preventer 142 that provide a fluidly sealed interface between the wellbore 108 and external environment, and into the wellbore 108 and formation 106. The rig 116 may also include a motorized winch 130 and other equipment for extending the tool string 112 into the wellbore 108, retrieving the tool string 112 from the wellbore 108, and positioning the tool string 112 at a selected depth within the wellbore 108.

While the operating environment shown in FIG. 1 relates to a stationary, land-based rig 116 for raising, lowering and setting the tool string 112, in alternative embodiments, mobile rigs, wellbore servicing units (such as coiled tubing units, slickline units, or wireline units), and the like may be used to lower the tool string 112. Further, while the operating environment is generally discussed as relating to a land-based well, the systems and methods described herein may instead be operated in subsea well configurations accessed by a fixed or floating platform. Further, while the downhole viscosity sensor 104 is shown as being deployed in a production environment, the downhole viscosity sensor 104 may be similarly deployed in a drilling environment during the formation of the wellbore 108.

In a production environment, as shown in FIG. 1, production fluids 146 are extracted from the formation 106 and delivered to the surface 132 via the wellbore 108. As fluid 146 is transported to the surface 132, the fluid passes through the blowout preventer 142 and a fluid diverter 144 that diverts fluid 146 to a collection tank 140 for subsequent processing and refinement. To facilitate diagnosis of the production fluid 146, the production fluid 146 may be routed through the downhole viscosity sensor 104 as it flows toward the surface 132. Similarly, during drilling operations, an operator may periodically analyze fluid from the wellbore 208 using a downhole viscosity sensor 204, as shown in FIG. 2.

Figure 2:
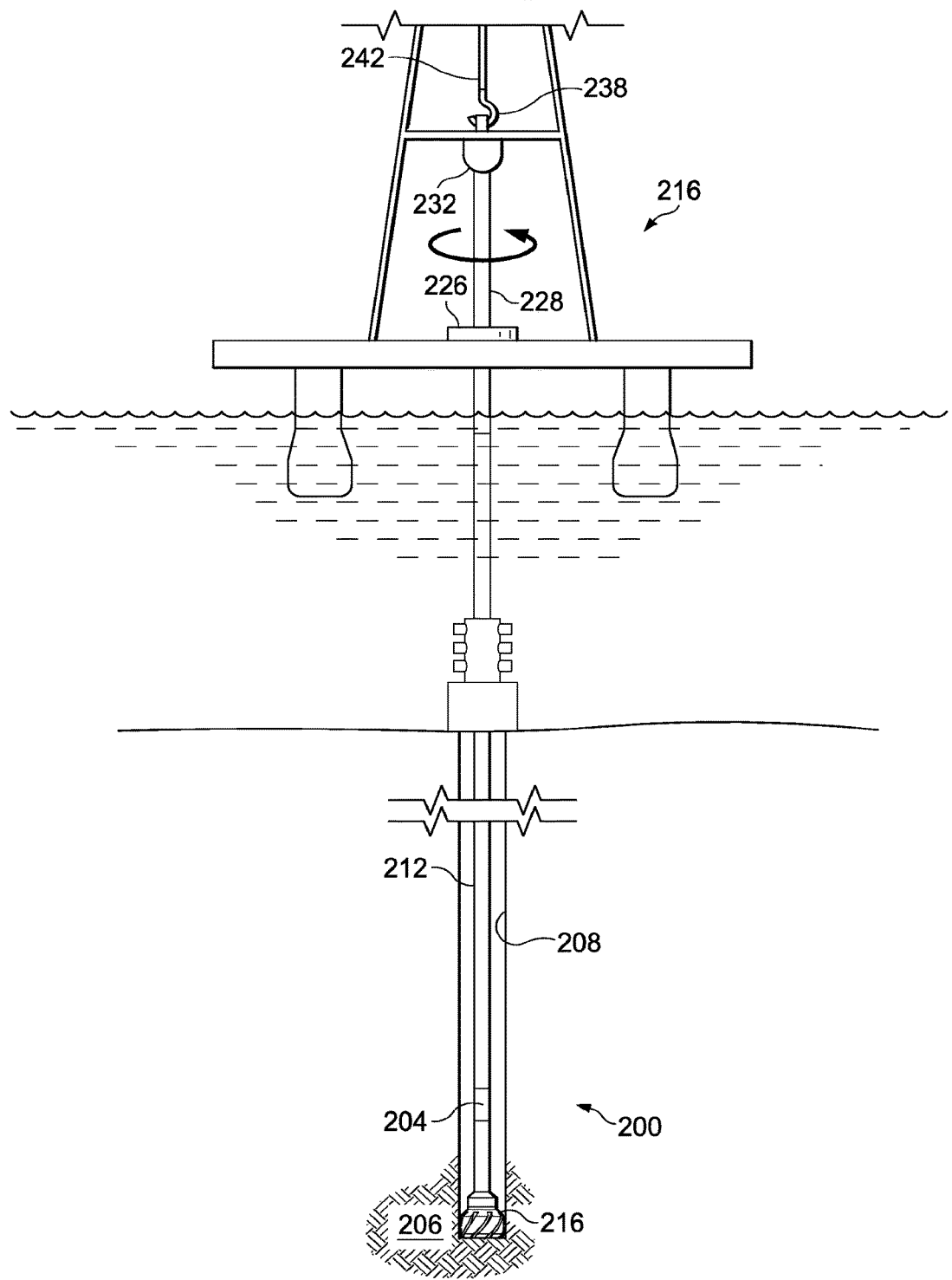
FIG. 2 illustrates a schematic view of a subsea well in which the system for determining the viscosity of a downhole fluid of FIG. 1 is deployed.

For example, FIG. 2 shows a subsea well 200 being formed from a formation 206 by an offshore drilling system 216. In the figure, the well 200 is being formed by a drill bit 216 that is suspended from a drill string 212 to form a wellbore 208. The drill string 212 may include or be coupled to a kelly 228, which may have a square, hexagonal or octagonal cross-section. The kelly 228 is connected at one end to the remainder of the drill string 212 and at an opposite end to a rotary swivel 232. The kelly 228 passes through a rotary table 226 that is capable of rotating the kelly and thus the remainder of the drill string 212 and drill bit 216. The rotary swivel 232 allows the kelly 228 to rotate without rotational motion being imparted above the rotary swivel 232. A hook 238, cable 242, traveling block (not shown), and hoist (not shown) are provided to lift or lower the drill bit 216, drill string 212, kelly 228 and rotary swivel 232 during drilling.

Figure 3:
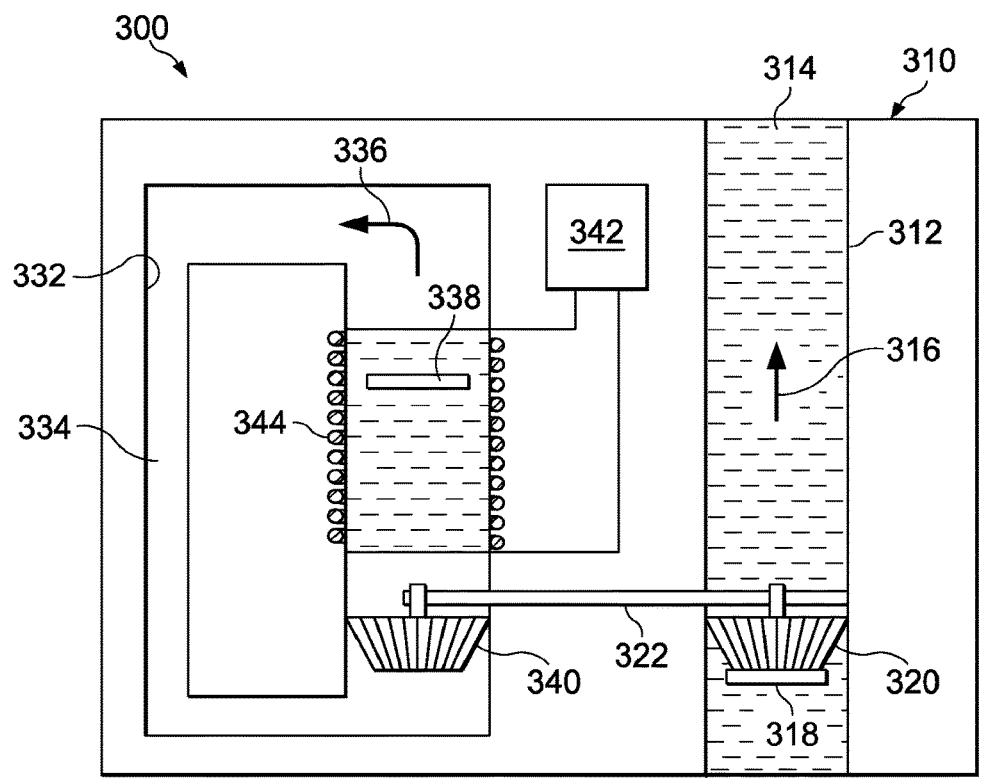
FIG. 3 is a schematic, sectional view of an illustrative embodiment of a system for determining the viscosity of a downhole fluid.

Referring now primarily to FIG. 3, an embodiment of a downhole viscosity sensor 300 that is analogous to the downhole viscosity sensor 104 is shown in schematic form. The downhole viscosity sensor 300 includes a first conduit 312, which may also be referred to as a first fluid flow path, through the sensor body 310. A production fluid 314 flows through the first conduit 312, which includes a turbine 320 or propeller and a velocity sensor 318, as indicated by the arrow 316 that indicates the direction of fluid flow. The downhole viscosity sensor 300 also includes a second conduit 332, which may be referred to as a second fluid flow path. The second conduit 332 includes a reference fluid 334, which may be a tunable fluid having variable viscosity, such as a magneto-rheological fluid or an electro-rheological fluid. The second conduit includes a second turbine 340, which is linked to the first turbine 320 by a mechanical or electrical coupling 322 that causes the second turbine 340 to rotate at the same rate as the first turbine 320. A second velocity sensor 338 is disposed along the second conduit 332 to measure the velocity of the reference fluid 334 as it is motivated by the second turbine 340.

Production fluid 314 flows through the first conduit 312 and first turbine 320, causing the first turbine to rotate. The coupling 322 causes the second turbine 340 to rotate at the same rate, which in turn causes the reference fluid 334 to flow within the second conduit 332, as indicated by the arrow 336. The downhole viscosity sensor 300 also a field generator 344 that is operable to generate an electric or magnetic field over all or a portion of the second conduit 312. To control the field generator 344 and gather and transmit data, the downhole viscosity sensor 300 may include an onboard controller 342.

Numerous fluids may be used as the reference fluid 334 provided the fluid allows the viscosity to be varied by the field generator 344. For example, the reference fluid 334 may be a magnetorheological fluid in an embodiment in which the field generator is a magnetic field generator. Similarly, the reference fluid 334 may be an electrorheological fluid in an embodiment in which the field generator is an electric field generator.

In other embodiments, the viscosity-tunable fluid may be an electro-rheological fluid and the field generator 344 may be an electric-field generator, wherein the strength of the electric-field is altered to manipulate the viscosity of the electrorheological fluid. In still further embodiments, the viscosity-tunable fluid may be an electromagneto-rheological fluid and the viscosity-control device an electromagnetic-field generator, wherein the strength of the electromagnetic field is altered to manipulate the viscosity of the combined electromagneto-rheological fluid.

Figure 4:
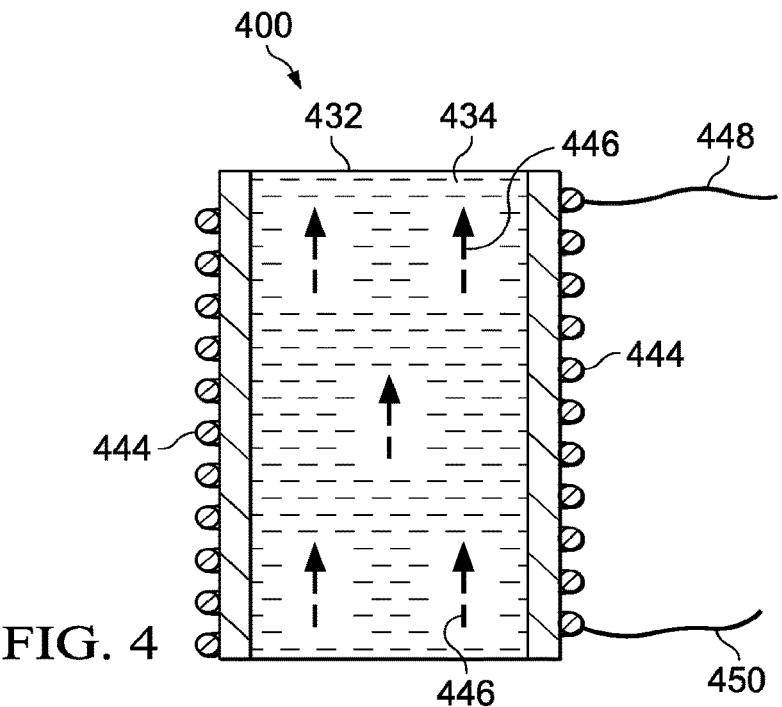
FIG. 4 is a schematic, sectional view of an illustrative magnetic field generator.

FIG. 4 shows an embodiment of a magnetic field generator 400 that may be used to vary the viscosity of the reference fluid 434. The magnetic field generator 400 includes a coil 444 that is wound around at least a portion of a conduit 432, which may be analogous to the second conduit 332 described above with regard to FIG. 3. A first end of the coil 444 is coupled to a potential 448 and a second end of the coil 444 is coupled to a ground 450. The magnitude of the potential 448 may be varied by a controller to generate a magnetic field 446 of varying magnitude that is applied across the conduit 432 to affect the rheological properties of the reference fluid 434 in an embodiment in which the reference fluid is a magnetorheological fluid. In such an embodiment, the strength of the magnetic field 446 may be varied by the controller to cause corresponding variations in the viscosity of the reference fluid 434.

In an embodiment, the magnetic-field generator 400 provides a unidirectional magnetic field 446 perpendicular to the longitudinal axis of the conduit 432. In another embodiment, a magnetic-field generator may include a permanent magnet, a Halbach array of permanent magnets, an alternative electromagnet, or another magnetic source operable to produce a pair of magnetic poles. In an embodiment in which a permanent magnet is used, permanent magnets may be positioned on each side of the conduit 432 and the conduit may be selectively shielded from or exposed to the permanent magnets to generate a magnetic field. Similarly, the extent to which the permanent magnet is shielded may be varied to vary the strength of the magnetic field. Such a shield may be created from a metallic material, such as, for example, a mu-metal and in such an embodiment, a permanent magnet enclosed within the shield may be placed adjacent the reference fluid 434 and gradually extended from the shield to increase the strength of the magnetic field and, as a result, the viscosity of the reference fluid 434. Alternative arrangements of magnets and electromagnets may also be used to selectively generate and vary the strength of a magnetic field.

Figure 5:
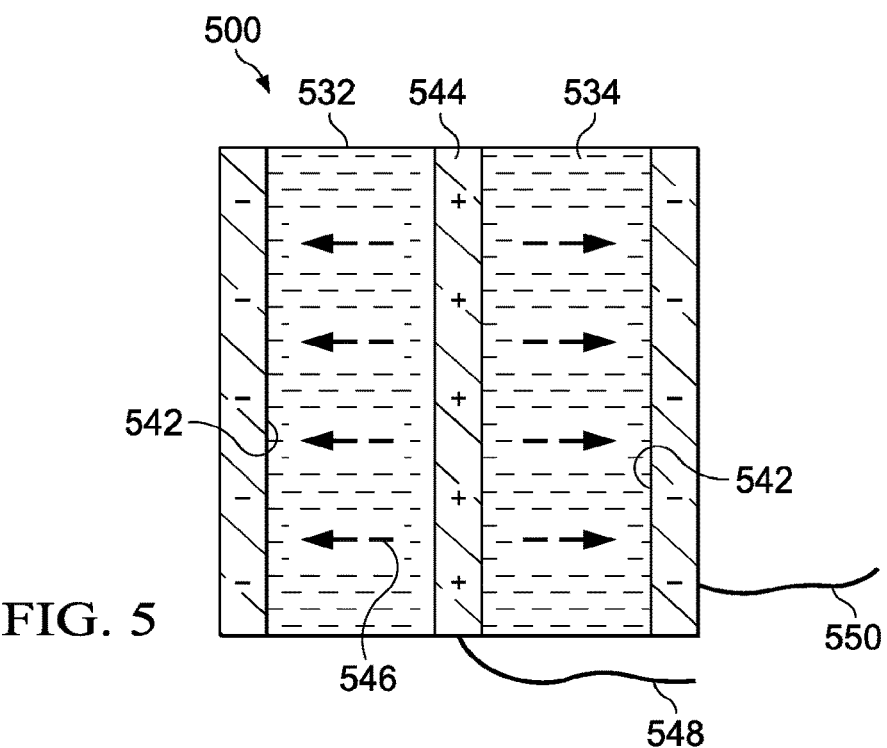
FIG. 5 is a schematic, sectional view of an illustrative electric field generator.

FIG. 5 shows an embodiment of an electric field generator 500 that may be used to vary the viscosity of the reference fluid 534 in an embodiment in which the reference fluid 534 is an electrorheological fluid. The electric field generator 500 includes first conductive surface 544 coupled to a potential 548 and a second conductive surface 542 coupled to a ground 550, though it is noted that in some embodiments, the first conductive surface may be coupled to the ground and the second conductive surface may be coupled to the potential. In an embodiment, the first conductive surface 544 is a wire or cylindrical element disposed within a conduit 532, which may be analogous to the second conduit 332 described above with regard to FIG. 3. In such an embodiment, the second conductive surface may be a conductive pipe, such as copper tubing, that covers all or a portion of the interior surface of the conduit 532. The magnitude of the potential 548 may be varied by a controller to generate an electric field 546 of varying magnitude that is applied across the conduit 532 to affect the rheological properties of the reference fluid 534. In such an embodiment, the strength of the electric field 546 may be varied by the controller to cause corresponding variations in the viscosity of the reference fluid 534.

Figure 6:
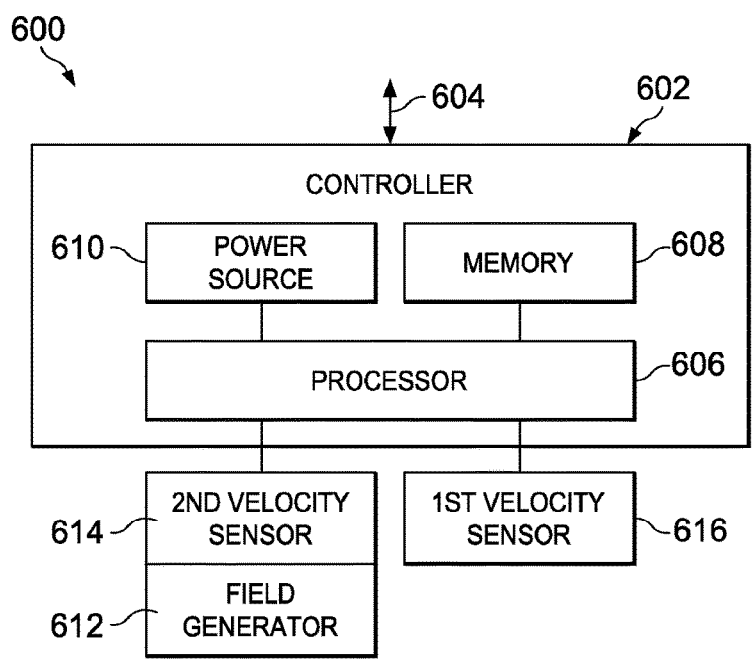
FIG. 6 is a block diagram, sectional view of an illustrative embodiment of a system for determining the viscosity of a downhole fluid.

FIG. 6 is a block diagram of a control system 600 for use in a downhole fluid viscosity sensor that is analogous to those described above, which is suitable for implementing the process described in FIG. 7 for estimating the viscosity of a production fluid. The control system includes a controller 602 having a processor 606 which is coupled to a memory 608 and a power source 610. The power source 610 may be a downhole power source, an onboard battery, a remote power source, or any other suitable power source. The controller 602 may also include a coupling 604, which may be a wired or wired coupling for transmitting data to a surface controller, receiving data from the surface controller, or receiving power from a remote power source to charge the power source 610, which may be an onboard battery. In an embodiment, the coupling 604 is a wired or wireless communications coupling. The controller 602 is coupled to a first velocity sensor 616, which may be analogous to the first velocity sensor described above with regard to FIG. 3, and a second velocity sensor 614, which may be analogous to the second velocity sensor described regard to FIG. 3. In addition, the controller 602 may be coupled to a field generator 612, which may be any of the field generators described above.

In an embodiment, the field generator 612 is disposed along a conduit of a downhole fluid viscosity sensor that includes a reference fluid to manipulate the viscosity of the reference fluid. The reference fluid may be a magnetorheological or electrorheological fluid, either of which may be referred to as a "smart" fluid. The controller 602 may include look-up tables, parameterized functional expressions, or artificial intelligence (e.g., neural networks, fuzzy logic, etc.) stored in memory 608 to enable the processor 606 to correlate the strength of the field generated by the field generator 612 to the viscosity of the reference fluid. In an illustrative process, the controller 602 may provide control signals to the field generator 612 to cause the field generator to increase or decrease the strength of the field. For example, in the process described below, the controller may analyze data received from velocity sensors, determine that the velocity of a reference fluid is slower than the velocity of the production fluid, and transmit a control signal to the field generator 612 to increase or decrease the strength of the field until the velocities are matched, at which point the controller may record or transmit to an operator the known viscosity of the reference fluid under the then-present operating conditions. As referenced herein, the operating conditions may include the magnitude of an electric or magnetic field generated by the field generator 612, in addition to the temperature and pressure conditions at the location of the reference fluid and production fluid. The controller 602 may therefore be coupled to a surface controller for communicating data to the surface and optionally receiving data or instructions from the surface.

FIG. 7 shows an illustrative process 700 for determining the viscosity of a fluid, such as a production fluid, flowing in a wellbore using a downhole fluid viscosity sensor in accordance with the embodiments described above. The method includes circulating a first fluid through a first fluid flow path 702. The first fluid flow path may have a turbine disposed therein that is rotated by the motion of the fluid therethrough. The method also includes circulating a second fluid through a second fluid flow path 704, where the second fluid has known rheological properties based on the condition in the second fluid flow path. A second turbine is disposed in the second fluid flow path and mechanically or electrically coupled to the first turbine in a way that results in the rotation of the first turbine causing the second turbine to rotate at the same rate as the first turbine. Using velocity sensors included in the first fluid flow path and second fluid flow path, the process includes determining the velocity of the first fluid 706, determining the velocity of the second fluid 708, and making a determination as to whether the first fluid velocity or flow rate matches the second fluid velocity 710. If the flow rates are determined to be the same, then the viscosity of the first fluid may be estimated from known properties of the second fluid 714. If the flow rates are determined to be different, then the viscosity of the second fluid may be increased 712, and the process 700 may be reiterated until the fluid velocity of the first fluid matches the fluid velocity of the second fluid.

The four response curves 802, 804, 806, and 808 of FIG. 8 demonstrate a correspondence between a strength of the applied magnetic field and a viscosity of the magneto-rheological fluid and illustrate how the flow characteristics of the reference fluid may be known based on the conditions of the reference fluid. As shown in FIG. 8, application of a magnetic field of specific magnitudes by a magnetic field generator permits the selection, in a predictable manner, of a viscosity of a magneto-rheological fluid. Control of the variable strength of the magnetic field and corresponding variance in viscosity of the magneto-rheological reference fluid therefore permits the magneto-rheological fluid to function as a viscosity-tunable reference fluid.

In FIG. 8, four fluid compositions are presented as non-limiting, representative examples of magneto-rheological fluids: a first composition including 20 wt. % carbonyl iron (CI) and fumed silica stabilizer ("Aerosil 200") in silicone oil (OKS 1050) shown by curve 802; a second composition including 40 wt. % carbonyl iron (CI) and fumed silica stabilizer ("Aerosil 200") in silicone oil (OKS 1050) shown by curve 804; a third composition including 20 wt. % carbonyl iron (CI) in silicone oil (OKS 1050) shown by curve 806; and a fourth composition including 40 wt. % carbonyl iron (CI) in silicone oil (OKS 1050) shown by curve 808. In each of the representative examples, the viscosity of the magneto-rheological fluid varies as a function of magnetic field strength generated by a field generator. A downhole viscosity sensor in accordance with the embodiments discussed above is thus operable to vary the viscosity of a magnetorheological reference fluid by varying the strength of a magnetic field applied to the reference fluid by a field generator. In an embodiment in which the reference fluid is an electrorheological fluid, the fluid may any suitable electrorheological fluid. In an illustrative embodiment, the electrorheological be formed from nanoparticles, such as polymer particles or particles of barium titanium oxalate, suspended in silicone-based oil.

In an embodiment, the viscosity of the second fluid may be decreased until the velocity of the first fluid matches the velocity of the second fluid. However, it may generally be preferable to commence the process 700 with the second fluid in a low viscosity state to minimize the effects of fluid drag on the system implementing the process. Thus, varying the viscosity of the second fluid until the velocity of the second fluid is equal to the velocity of the first fluid may generally involve circulating the second fluid in a low viscosity state and gradually increasing the viscosity of the second fluid until the velocities of the fluids match.

As described with regard to the systems and apparatuses discussed above, circulating the second fluid through the second fluid flow path may comprise recirculating a reference fluid in the second fluid flow path.

In an embodiment, the first fluid may be a fluid received from a formation and circulating the first fluid through the first fluid flow path may include receiving a production fluid from the formation and circulating the production fluid through the first fluid flow path.

In an embodiment, the second fluid may be an electrorheological fluid, and varying the viscosity of the second fluid may be accomplished by applying a variable strength electric field to the second fluid. In such an embodiment, applying the variable strength electric field to the second fluid may involve applying a variable potential to a capacitive structure that applies an electric field to at least a portion of the second fluid flow path. The capacitive structure may be a first conductive surface and a second conductive surface place in contact with the second fluid, with one of the surface coupled to a potential and the other coupled to a ground.

In another embodiment, the second fluid may be a magnetorheological fluid and varying the viscosity of the second fluid may involve applying a variable strength magnetic field to the second fluid. This may be accomplished by applying a variable-strength current to a coil that surrounds at least a portion of the second fluid flow path.

To implement the processes described above, in an illustrative embodiment, a downhole viscosity sensor includes a first fluid flow path including a turbine and a velocity sensor and a second fluid flow path including a second turbine and a second velocity sensor. A mechanical linkage links the first turbine and second turbine. The sensor also includes a field generator that is capable of generating, for example, an electric or magnetic field. The first fluid flow path forms an open flow path for receiving a fluid from a formation and the second fluid flow path forms a closed flow path enclosing a reference fluid having a variable viscosity.

In an embodiment, the reference fluid is an electrorheological fluid and the field generator is an electric field generator. The electric field generator is coupled to a potential and a ground, and to a controller. The controller may provide the potential and may therefore be operable to control the magnitude of the electric field generated by the electric field generator.

In another embodiment, the reference fluid is a magnetorheological fluid, and the field generator is a magnetic field generator. The magnetic field generator may be formed by a permanent magnet, an array of magnets, or an electromagnet. In an embodiment in which the magnetic field generator includes an electromagnet, the generator may be formed from a coil wrapped about a portion of the second fluid flow path.

According to another illustrative embodiment, a system for sensing the viscosity of a production fluid includes a downhole viscosity sensor having a first fluid flow path that includes a turbine and a velocity sensor disposed along the flow path. The sensor also includes a second fluid flow path that has a second turbine and a second velocity sensor disposed along the second flow path. A mechanical linkage couples the first turbine and second turbine so that they will rotate in unison. In an illustrative embodiment, the first fluid flow path is an open flow path for receiving a production fluid from a formation and the second fluid flow path is a closed flow path having a reference fluid recirculated therein. A controller is communicatively coupled to the downhole viscosity sensor. The controller is operable to communicate a control signal to the downhole viscosity sensor; and the downhole viscosity sensor is operable to vary the viscosity of the reference fluid in response to the control signal.

In an embodiment, the reference fluid is an electrorheological fluid and the second fluid flow path comprises an electric field generator, which may be a capacitive structure having conductive surfaces of different potentials on either side of the fluid flow path. In an embodiment, the capacitive structure comprises a plate capacitor having a variable potential on a first side of the first fluid flow path and a second capacitive plate on a second, opposing side of the second fluid flow path, the second capacitive plate being electrically coupled to a ground. In an embodiment, the capacitor is formed from a wire having a variable potential disposed within the second fluid flow path and a conductive casing enclosing the second fluid flow path, the conductive casing being electrically coupled to a ground. In another embodiment, the capacitor comprises a conductive casing having a variable potential enclosing the second fluid flow path and a wire disposed within the first fluid flow path, and the wire is electrically coupled to a ground.

In an embodiment, the reference fluid is be a magnetorheological fluid and the second fluid flow path includes a magnetic field generator across all or a portion of the second fluid flow path. The magnetic field generator may be a capacitor, a permanent magnet, or an electromagnet, such as a magnetic coil or an electromagnetic plate adjacent the first fluid flow path.

In an embodiment, a representative system includes a memory, a power source, and a processor. The memory comprises instructions to cause the processor to receive a first fluid velocity measurement indicating the velocity of the production fluid in the first fluid flow path, receiving a second fluid velocity measurement indicating the velocity of the reference fluid, and varying the strength of an electric field applied to the reference fluid until the velocity of the reference fluid is equivalent to the velocity of the production fluid.

In an embodiment, a memory includes instructions to cause the processor to receive a first fluid velocity measurement indicating the velocity of the production fluid, receiving a second fluid velocity measurement indicating the velocity of the reference fluid in the second fluid flow path, and vary the strength of a magnetic field applied to the reference fluid until the velocity of the reference fluid is equivalent to the velocity of the production fluid.

In addition to the illustrative embodiments described above, many examples of specific combinations are within the scope of the disclosure, some of which are presented below.

Example One

A downhole viscosity sensor having a first fluid flow path that includes a turbine and a velocity sensor and a second fluid flow path that includes a second turbine and a second velocity sensor. The downhole viscosity sensor further includes a mechanical linkage linking the first turbine and second turbine and a field generator. The fluid flow path is an open flow path for receiving a fluid from a formation and second fluid flow is a closed flow path having a reference fluid. The reference fluid is a variable viscosity, such as an electrorheological fluid or a magnetorheological fluid.

Example Two

A downhole viscosity sensor having a first fluid flow path that includes a turbine and a velocity sensor and a second fluid flow path that includes a second turbine and a second velocity sensor. The downhole viscosity sensor further includes a mechanical linkage linking the first turbine and second turbine and a field generator. The fluid flow path is an open flow path for receiving a fluid from a formation and second fluid flow is a closed flow path having a reference fluid. The reference fluid is an electrorheological fluid and the field generator is an electric field generator.

Example Three

A downhole viscosity sensor having a first fluid flow path that includes a turbine and a velocity sensor and a second fluid flow path that includes a second turbine and a second velocity sensor. The downhole viscosity sensor further includes a mechanical linkage linking the first turbine and second turbine and a field generator. The fluid flow path is an open flow path for receiving a fluid from a formation and second fluid flow is a closed flow path having a reference fluid. The reference fluid is an electrorheological fluid and the field generator is an electric field generator, which is coupled to a potential and a ground.

Example Four

A downhole viscosity sensor having a first fluid flow path that includes a turbine and a velocity sensor and a second fluid flow path that includes a second turbine and a second velocity sensor. The downhole viscosity sensor further includes a mechanical linkage linking the first turbine and second turbine and a field generator. The fluid flow path is an open flow path for receiving a fluid from a formation and second fluid flow is a closed flow path having a reference fluid. The reference fluid is an electrorheological fluid and the field generator is an electric field generator, which is coupled to a potential and a ground. The downhole viscosity sensor further comprises a controller coupled to the potential and operable to control the magnitude of the potential.

Example Five

A downhole viscosity sensor having a first fluid flow path that includes a turbine and a velocity sensor and a second fluid flow path that includes a second turbine and a second velocity sensor. The downhole viscosity sensor further includes a mechanical linkage linking the first turbine and second turbine and a field generator. The fluid flow path is an open flow path for receiving a fluid from a formation and second fluid flow is a closed flow path having a reference fluid. The reference fluid is a magnetorheological fluid.

Example Six

A downhole viscosity sensor having a first fluid flow path that includes a turbine and a velocity sensor and a second fluid flow path that includes a second turbine and a second velocity sensor. The downhole viscosity sensor further includes a mechanical linkage linking the first turbine and second turbine and a field generator. The fluid flow path is an open flow path for receiving a fluid from a formation and second fluid flow is a closed flow path having a reference fluid. The reference fluid is a magnetorheological fluid and the field generator is a magnetic field generator.

Example Seven

A downhole viscosity sensor having a first fluid flow path that includes a turbine and a velocity sensor and a second fluid flow path that includes a second turbine and a second velocity sensor. The downhole viscosity sensor further includes a mechanical linkage linking the first turbine and second turbine and a field generator. The fluid flow path is an open flow path for receiving a fluid from a formation and second fluid flow is a closed flow path having a reference fluid. The reference fluid is a magnetorheological fluid and the field generator is a magnetic field generator. In this example, the magnetic field generator is a coil wrapped about a portion of the second fluid flow path.

Example Eight

A method for determining the viscosity of a fluid in a wellbore that includes circulating a first fluid through a first fluid flow path having a turbine disposed therein, and circulating a second fluid through a second fluid flow path having a second turbine disposed therein. The second turbine is mechanically linked to the first turbine. The method also includes determining the velocity of the first fluid circulating through the first fluid flow path; determining the velocity of the second fluid circulating through the second fluid flow path; varying the viscosity of the second fluid until the velocity of the second fluid is approximately equal to the velocity of the first fluid; and estimating the viscosity of the first fluid based on known rheological properties of the first fluid.

Example Nine

A method for determining the viscosity of a fluid in a wellbore that includes circulating a first fluid through a first fluid flow path having a turbine disposed therein, and circulating a second fluid through a second fluid flow path having a second turbine disposed therein. The second turbine is mechanically linked to the first turbine. The method also includes determining the velocity of the first fluid circulating through the first fluid flow path; determining the velocity of the second fluid circulating through the second fluid flow path; varying the viscosity of the second fluid until the velocity of the second fluid is approximately equal to the velocity of the first fluid; and estimating the viscosity of the first fluid based on known rheological properties of the first fluid. In this example, circulating the second fluid through a second fluid flow path comprises recirculating a reference fluid in the second fluid flow path.

Example Ten

A method for determining the viscosity of a fluid in a wellbore that includes circulating a first fluid through a first fluid flow path having a turbine disposed therein, and circulating a second fluid through a second fluid flow path having a second turbine disposed therein. The second turbine is mechanically linked to the first turbine. The method also includes determining the velocity of the first fluid circulating through the first fluid flow path; determining the velocity of the second fluid circulating through the second fluid flow path; varying the viscosity of the second fluid until the velocity of the second fluid is approximately equal to the velocity of the first fluid; and estimating the viscosity of the first fluid based on known rheological properties of the first fluid. In this example circulating the second fluid through a second fluid flow path comprises recirculating a reference fluid in the second fluid flow path. Here, the first fluid is a fluid received from a formation and circulating the first fluid through the first fluid flow path involves receiving fluid from the formation and circulating the first fluid through the first fluid flow path.

Example Eleven

A method for determining the viscosity of a fluid in a wellbore that includes circulating a first fluid through a first fluid flow path having a turbine disposed therein, and circulating a second fluid through a second fluid flow path having a second turbine disposed therein. The second turbine is mechanically linked to the first turbine. The method also includes determining the velocity of the first fluid circulating through the first fluid flow path; determining the velocity of the second fluid circulating through the second fluid flow path; varying the viscosity of the second fluid until the velocity of the second fluid is approximately equal to the velocity of the first fluid; and estimating the viscosity of the first fluid based on known rheological properties of the first fluid. In this example circulating the second fluid through a second fluid flow path comprises recirculating a reference fluid in the second fluid flow path. The second fluid is an electrorheological fluid and varying the viscosity of the second fluid involves applying a variable strength electric field to the second fluid.

Example Twelve

A method for determining the viscosity of a fluid in a wellbore that includes circulating a first fluid through a first fluid flow path having a turbine disposed therein, and circulating a second fluid through a second fluid flow path having a second turbine disposed therein. The second turbine is mechanically linked to the first turbine. The method also includes determining the velocity of the first fluid circulating through the first fluid flow path; determining the velocity of the second fluid circulating through the second fluid flow path; varying the viscosity of the second fluid until the velocity of the second fluid is approximately equal to the velocity of the first fluid; and estimating the viscosity of the first fluid based on known rheological properties of the first fluid. In this example circulating the second fluid through a second fluid flow path comprises recirculating a reference fluid in the second fluid flow path. The second fluid is an electrorheological fluid and varying the viscosity of the second fluid involves applying a variable strength electric field to the second fluid. Applying the variable strength electric field to the second fluid includes applying a variable potential to a capacitive structure that applies an electric field to at least a portion of the second fluid flow path.

Example Thirteen

A method for determining the viscosity of a fluid in a wellbore that includes circulating a first fluid through a first fluid flow path having a turbine disposed therein, and circulating a second fluid through a second fluid flow path having a second turbine disposed therein. The second turbine is mechanically linked to the first turbine. The method also includes determining the velocity of the first fluid circulating through the first fluid flow path; determining the velocity of the second fluid circulating through the second fluid flow path; varying the viscosity of the second fluid until the velocity of the second fluid is approximately equal to the velocity of the first fluid; and estimating the viscosity of the first fluid based on known rheological properties of the first fluid. The second fluid is a magnetorheological fluid and varying the viscosity of the second fluid involves applying a variable strength magnetic field to the second fluid.

Example Fourteen

A method for determining the viscosity of a fluid in a wellbore that includes circulating a first fluid through a first fluid flow path having a turbine disposed therein, and circulating a second fluid through a second fluid flow path having a second turbine disposed therein. The second turbine is mechanically linked to the first turbine. The method also includes determining the velocity of the first fluid circulating through the first fluid flow path; determining the velocity of the second fluid circulating through the second fluid flow path; varying the viscosity of the second fluid until the velocity of the second fluid is approximately equal to the velocity of the first fluid; and estimating the viscosity of the first fluid based on known rheological properties of the first fluid. The second fluid is a magnetorheological fluid and varying the viscosity of the second fluid involves applying a variable strength magnetic field to the second fluid. Applying the variable strength magnetic field to the second fluid involves applying a variable current to a coil that surrounds at least a portion of the second fluid flow path.

Example Fifteen

A method for determining the viscosity of a fluid in a wellbore that includes circulating a first fluid through a first fluid flow path having a turbine disposed therein, and circulating a second fluid through a second fluid flow path having a second turbine disposed therein. The second turbine is mechanically linked to the first turbine. The method also includes determining the velocity of the first fluid circulating through the first fluid flow path; determining the velocity of the second fluid circulating through the second fluid flow path; varying the viscosity of the second fluid until the velocity of the second fluid is approximately equal to the velocity of the first fluid; and estimating the viscosity of the first fluid based on known rheological properties of the first fluid. Varying the viscosity of the second fluid until the velocity of the second fluid is approximately equal to the velocity of the first fluid involves circulating the second fluid in a low viscosity state and gradually increasing the viscosity of the second fluid.

Example Sixteen

A system for sensing the viscosity of a production fluid includes a downhole viscosity sensor having a first fluid flow path that includes a turbine and a velocity sensor, in addition to a second fluid flow path that includes a second turbine and a second velocity sensor, and a mechanical linkage linking the first turbine and second turbine. The first fluid flow path is an open flow path for receiving a production fluid from a formation and the second fluid flow path being a closed flow path having a reference fluid disposed therein. The system also includes a controller communicatively coupled to the downhole viscosity sensor. The controller is operable to communicate a control signal to the downhole viscosity sensor, and the downhole viscosity sensor is operable to vary the viscosity of the reference fluid in response to the control signal.

Example Seventeen

A system for sensing the viscosity of a production fluid includes a downhole viscosity sensor having a first fluid flow path that includes a turbine and a velocity sensor, in addition to a second fluid flow path that includes a second turbine and a second velocity sensor, and a mechanical linkage linking the first turbine and second turbine. The first fluid flow path is an open flow path for receiving a production fluid from a formation and the second fluid flow path being a closed flow path having a reference fluid disposed therein. The system also includes a controller communicatively coupled to the downhole viscosity sensor. The controller is operable to communicate a control signal to the downhole viscosity sensor, and the downhole viscosity sensor is operable to vary the viscosity of the reference fluid in response to the control signal. The reference fluid is an electrorheological fluid.

Example Eighteen

A system for sensing the viscosity of a production fluid includes a downhole viscosity sensor having a first fluid flow path that includes a turbine and a velocity sensor, in addition to a second fluid flow path that includes a second turbine and a second velocity sensor, and a mechanical linkage linking the first turbine and second turbine. The first fluid flow path is an open flow path for receiving a production fluid from a formation and the second fluid flow path being a closed flow path having a reference fluid disposed therein. The system also includes a controller communicatively coupled to the downhole viscosity sensor. The controller is operable to communicate a control signal to the downhole viscosity sensor, and the downhole viscosity sensor is operable to vary the viscosity of the reference fluid in response to the control signal. The reference fluid is an electrorheological fluid and the second fluid flow path is an electric field generator.

Example Nineteen

A system for sensing the viscosity of a production fluid includes a downhole viscosity sensor having a first fluid flow path that includes a turbine and a velocity sensor, in addition to a second fluid flow path that includes a second turbine and a second velocity sensor, and a mechanical linkage linking the first turbine and second turbine. The first fluid flow path is an open flow path for receiving a production fluid from a formation and the second fluid flow path being a closed flow path having a reference fluid disposed therein. The system also includes a controller communicatively coupled to the downhole viscosity sensor. The controller is operable to communicate a control signal to the downhole viscosity sensor, and the downhole viscosity sensor is operable to vary the viscosity of the reference fluid in response to the control signal. The reference fluid is an electrorheological fluid and the second fluid flow path is an electric field generator, which includes a capacitor.

Example Twenty

A system for sensing the viscosity of a production fluid includes a downhole viscosity sensor having a first fluid flow path that includes a turbine and a velocity sensor, in addition to a second fluid flow path that includes a second turbine and a second velocity sensor, and a mechanical linkage linking the first turbine and second turbine. The first fluid flow path is an open flow path for receiving a production fluid from a formation and the second fluid flow path being a closed flow path having a reference fluid disposed therein. The system also includes a controller communicatively coupled to the downhole viscosity sensor. The controller is operable to communicate a control signal to the downhole viscosity sensor, and the downhole viscosity sensor is operable to vary the viscosity of the reference fluid in response to the control signal. The reference fluid is an electrorheological fluid and the second fluid flow path is an electric field generator, which includes a capacitor. The capacitor includes a plate capacitor having a capacitive plate having a variable potential on a first side of the first fluid flow path and a second capacitive plate on a second, opposing side of the second fluid flow path, with the second capacitive plate being electrically coupled to a ground.

Example Twenty-One

A system for sensing the viscosity of a production fluid includes a downhole viscosity sensor having a first fluid flow path that includes a turbine and a velocity sensor, in addition to a second fluid flow path that includes a second turbine and a second velocity sensor, and a mechanical linkage linking the first turbine and second turbine. The first fluid flow path is an open flow path for receiving a production fluid from a formation and the second fluid flow path being a closed flow path having a reference fluid disposed therein. The system also includes a controller communicatively coupled to the downhole viscosity sensor. The controller is operable to communicate a control signal to the downhole viscosity sensor, and the downhole viscosity sensor is operable to vary the viscosity of the reference fluid in response to the control signal. The reference fluid is an electrorheological fluid and the second fluid flow path is an electric field generator, which includes a capacitor. The capacitor includes a wire having a variable potential disposed within the second fluid flow path and a conductive casing enclosing the second fluid flow path, the conductive casing being electrically coupled to a ground.

Example Twenty-Two

A system for sensing the viscosity of a production fluid includes a downhole viscosity sensor having a first fluid flow path that includes a turbine and a velocity sensor, in addition to a second fluid flow path that includes a second turbine and a second velocity sensor, and a mechanical linkage linking the first turbine and second turbine. The first fluid flow path is an open flow path for receiving a production fluid from a formation and the second fluid flow path being a closed flow path having a reference fluid disposed therein. The system also includes a controller communicatively coupled to the downhole viscosity sensor. The controller is operable to communicate a control signal to the downhole viscosity sensor, and the downhole viscosity sensor is operable to vary the viscosity of the reference fluid in response to the control signal. The reference fluid is an electrorheological fluid and the second fluid flow path is an electric field generator, which includes a capacitor. The capacitor includes a conductive casing having a variable potential enclosing the second fluid flow path and a wire disposed within the first fluid flow path that is electrically coupled to a ground.

Example Twenty-Three

A system for sensing the viscosity of a production fluid includes a downhole viscosity sensor having a first fluid flow path that includes a turbine and a velocity sensor, in addition to a second fluid flow path that includes a second turbine and a second velocity sensor, and a mechanical linkage linking the first turbine and second turbine. The first fluid flow path is an open flow path for receiving a production fluid from a formation and the second fluid flow path being a closed flow path having a reference fluid disposed therein. The system also includes a controller communicatively coupled to the downhole viscosity sensor. The controller is operable to communicate a control signal to the downhole viscosity sensor, and the downhole viscosity sensor is operable to vary the viscosity of the reference fluid in response to the control signal. The reference fluid is a magnetorheological fluid.

Example Twenty-Four

A system for sensing the viscosity of a production fluid includes a downhole viscosity sensor having a first fluid flow path that includes a turbine and a velocity sensor, in addition to a second fluid flow path that includes a second turbine and a second velocity sensor, and a mechanical linkage linking the first turbine and second turbine. The first fluid flow path is an open flow path for receiving a production fluid from a formation and the second fluid flow path being a closed flow path having a reference fluid disposed therein. The system also includes a controller communicatively coupled to the downhole viscosity sensor. The controller is operable to communicate a control signal to the downhole viscosity sensor, and the downhole viscosity sensor is operable to vary the viscosity of the reference fluid in response to the control signal. The reference fluid is a magnetorheological fluid and the second fluid flow path includes a magnetic field generator.

Example Twenty-Five

A system for sensing the viscosity of a production fluid includes a downhole viscosity sensor having a first fluid flow path that includes a turbine and a velocity sensor, in addition to a second fluid flow path that includes a second turbine and a second velocity sensor, and a mechanical linkage linking the first turbine and second turbine. The first fluid flow path is an open flow path for receiving a production fluid from a formation and the second fluid flow path being a closed flow path having a reference fluid disposed therein. The system also includes a controller communicatively coupled to the downhole viscosity sensor. The controller is operable to communicate a control signal to the downhole viscosity sensor, and the downhole viscosity sensor is operable to vary the viscosity of the reference fluid in response to the control signal. The reference fluid is a magnetorheological fluid and the second fluid flow path includes a magnetic field generator, which is an electromagnet.

Example Twenty-Six

A system for sensing the viscosity of a production fluid includes a downhole viscosity sensor having a first fluid flow path that includes a turbine and a velocity sensor, in addition to a second fluid flow path that includes a second turbine and a second velocity sensor, and a mechanical linkage linking the first turbine and second turbine. The first fluid flow path is an open flow path for receiving a production fluid from a formation and the second fluid flow path being a closed flow path having a reference fluid disposed therein. The system also includes a controller communicatively coupled to the downhole viscosity sensor. The controller is operable to communicate a control signal to the downhole viscosity sensor, and the downhole viscosity sensor is operable to vary the viscosity of the reference fluid in response to the control signal. The reference fluid is a magnetorheological fluid and the second fluid flow path includes a magnetic field generator that is an electromagnetic coil that surrounds at least a portion of the second fluid flow path.

Example Twenty-Seven

A system for sensing the viscosity of a production fluid includes a downhole viscosity sensor having a first fluid flow path that includes a turbine and a velocity sensor, in addition to a second fluid flow path that includes a second turbine and a second velocity sensor, and a mechanical linkage linking the first turbine and second turbine. The first fluid flow path is an open flow path for receiving a production fluid from a formation and the second fluid flow path being a closed flow path having a reference fluid disposed therein. The system also includes a controller communicatively coupled to the downhole viscosity sensor. The controller is operable to communicate a control signal to the downhole viscosity sensor, and the downhole viscosity sensor is operable to vary the viscosity of the reference fluid in response to the control signal. The reference fluid is a magnetorheological fluid and the second fluid flow path includes a magnetic field generator, which is an electromagnetic plate adjacent the second fluid flow path.

Example Twenty-Eight

A system for sensing the viscosity of a production fluid includes a downhole viscosity sensor having a first fluid flow path that includes a turbine and a velocity sensor, in addition to a second fluid flow path that includes a second turbine and a second velocity sensor, and a mechanical linkage linking the first turbine and second turbine. The first fluid flow path is an open flow path for receiving a production fluid from a formation and the second fluid flow path being a closed flow path having a reference fluid disposed therein. The system also includes a controller communicatively coupled to the downhole viscosity sensor. The controller is operable to communicate a control signal to the downhole viscosity sensor, and the downhole viscosity sensor is operable to vary the viscosity of the reference fluid in response to the control signal. The reference fluid is a magnetorheological fluid and the second fluid flow path includes a magnetic field generator. The controller is a memory, a power source, and a processor.

Example Twenty-Nine

A system for sensing the viscosity of a production fluid includes a downhole viscosity sensor having a first fluid flow path that includes a turbine and a velocity sensor, in addition to a second fluid flow path that includes a second turbine and a second velocity sensor, and a mechanical linkage linking the first turbine and second turbine. The first fluid flow path is an open flow path for receiving a production fluid from a formation and the second fluid flow path being a closed flow path having a reference fluid disposed therein. The system also includes a controller communicatively coupled to the downhole viscosity sensor. The controller is operable to communicate a control signal to the downhole viscosity sensor, and the downhole viscosity sensor is operable to vary the viscosity of the reference fluid in response to the control signal. The reference fluid is a magnetorheological fluid and the second fluid flow path includes a magnetic field generator. The controller is a memory, a power source, and a processor. The memory includes instructions to cause the processor to receive a first fluid velocity measurement indicating the velocity of the production fluid in the first fluid flow path, to receive a second fluid velocity measurement indicating the velocity of the reference fluid, and to generate a control signal that varies the strength of an electric field applied to the reference fluid until the velocity of the reference fluid is equivalent to the velocity of the production fluid.

Example Thirty

A system for sensing the viscosity of a production fluid includes a downhole viscosity sensor having a first fluid flow path that includes a turbine and a velocity sensor, in addition to a second fluid flow path that includes a second turbine and a second velocity sensor, and a mechanical linkage linking the first turbine and second turbine. The first fluid flow path is an open flow path for receiving a production fluid from a formation and the second fluid flow path being a closed flow path having a reference fluid disposed therein. The system also includes a controller communicatively coupled to the downhole viscosity sensor. The controller is operable to communicate a control signal to the downhole viscosity sensor, and the downhole viscosity sensor is operable to vary the viscosity of the reference fluid in response to the control signal. The reference fluid is a magnetorheological fluid and the second fluid flow path includes a magnetic field generator. The controller is a memory, a power source, and a processor. The memory includes instructions to cause the processor to receive a first fluid velocity measurement indicating the velocity of the production fluid, to receive a second fluid velocity measurement indicating the velocity of the reference fluid in the second fluid flow path, and to generate a control signal to vary the strength of a magnetic field applied to the reference fluid until the velocity of the reference fluid is equivalent to the velocity of the production fluid.

It will be understood that the above description of preferred embodiments is given by way of example only and that various modifications may be made by those skilled in the art. The above specification, examples, and data provide a complete description of the structure and use of exemplary embodiments of the invention. Although various embodiments of the invention have been described above with a certain degree of particularity, or with reference to one or more individual embodiments, those skilled in the art could make numerous alterations to the disclosed embodiments without departing from the scope of the claims.

We claim:
1. A downhole viscosity sensor comprising:
   a first fluid flow path including a turbine and a velocity sensor;
   a second fluid flow path including a second turbine and a second velocity sensor;
   a mechanical linkage linking the first turbine and second turbine; and
   a field generator;
   wherein the first fluid flow path comprises an open flow path for receiving a fluid from a formation; and
   wherein the second fluid flow path comprises a closed flow path having a reference fluid, the reference fluid having a variable viscosity.
2. The downhole viscosity sensor of claim 1, wherein the reference fluid comprises an electrorheological fluid and the field generator comprises an electric field generator.
3. The downhole viscosity sensor of claim 1, further comprising a controller coupled to a potential and operable to control the magnitude of the potential.
4. The downhole viscosity sensor of claim 1, wherein the reference fluid comprises a magnetorheological fluid and wherein the field generator comprises a magnetic field generator.
5. The downhole viscosity sensor of claim 4, wherein the magnetic field generator comprises a coil wrapped about a portion of the second fluid flow path.

6. A method of determining the viscosity of a fluid in a wellbore, the method comprising:
 circulating a first fluid through a first fluid flow path having a turbine disposed therein;
 circulating a second fluid through a second fluid flow path having a second turbine disposed therein, the second turbine being mechanically linked to the first turbine;
 determining the velocity of the first fluid circulating through the first fluid flow path;
 determining the velocity of the second fluid circulating through the second fluid flow path;
 varying the viscosity of the second fluid until the velocity of the second fluid is approximately equal to the velocity of the first fluid; and
 estimating the viscosity of the first fluid based on known rheological properties of the first fluid.

7. The method of claim 6, wherein the first fluid comprises a fluid received from a formation and wherein circulating the first fluid through the first fluid flow path comprises receiving fluid from the formation and circulating the first fluid through the first fluid flow path.

8. The method of claim 6, wherein the second fluid comprises an electrorheological fluid, and wherein varying the viscosity of the second fluid comprises applying a variable strength electric field to the second fluid.

9. The method of claim 8, wherein applying the variable strength electric field to the second fluid comprises applying a variable potential to a capacitive structure that applies an electric field to at least a portion of the second fluid flow path.

10. The method of claim 6, wherein the second fluid comprises a magnetorheological fluid, and wherein varying the viscosity of the second fluid comprises applying a variable strength magnetic field to the second fluid.

11. The method of claim 10, wherein applying the variable strength magnetic field to the second fluid comprises applying a variable current to a coil that surrounds at least a portion of the second fluid flow path.

12. The method of claim 6, wherein varying the viscosity of the second fluid until the velocity of the second fluid is approximately equal to the velocity of the first fluid comprises circulating the second fluid in a low viscosity state and gradually increasing the viscosity of the second fluid.

13. A system to sense the viscosity of a production fluid, the system comprising:
 a downhole viscosity sensor having a first fluid flow path including a turbine and a velocity sensor, a second fluid flow path including a second turbine and a second velocity sensor, and a mechanical linkage linking the first turbine and second turbine, the first fluid flow path being an open flow path for receiving a production fluid from a formation and the second fluid flow path being a closed flow path having a reference fluid;
 a controller communicatively coupled to the downhole viscosity sensor;
 wherein the controller is operable to communicate a control signal to the downhole viscosity sensor; and
 wherein the downhole viscosity sensor is operable to vary the viscosity of the reference fluid in response to the control signal.

14. The system of claim 13, wherein the reference fluid comprises an electrorheological fluid and wherein the second fluid flow path comprises an electric field generator.

15. The system of claim 14, wherein the electric field generator comprises a capacitor.

16. The system of claim 15, wherein the capacitor comprises a plate capacitor having a capacitive plate having a variable potential on a first side of the first fluid flow path and a second capacitive plate on a second, opposing side of the second fluid flow path, the second capacitive plate being electrically coupled to a ground.

17. The system of claim 15, wherein the capacitor comprises a wire having a variable potential disposed within the second fluid flow path and a conductive casing enclosing the second fluid flow path, the conductive casing being electrically coupled to a ground.

18. The system of claim 13, wherein the reference fluid comprises a magnetorheological fluid and wherein the second fluid flow path comprises a magnetic field generator.

19. The system of claim 18, wherein the electromagnet comprises an electromagnetic coil that surrounds at least a portion of the second fluid flow path.

20. The system of claim 19, wherein the controller comprises a memory, a power source, and a processor, and wherein the memory comprises instructions to cause the processor to receive a first fluid velocity measurement indicating the velocity of the production fluid, to receive a second fluid velocity measurement indicating the velocity of the reference fluid in the second fluid flow path, and to generate a control signal to vary the strength of a magnetic field applied to the reference fluid until the velocity of the reference fluid is equivalent to the velocity of the production fluid.

* * * * *